United States Patent
Rittmann et al.

(10) Patent No.: US 11,306,280 B2
(45) Date of Patent: Apr. 19, 2022

(54) SYSTEMS AND METHODS OF ATMOSPHERIC CARBON DIOXIDE ENRICHMENT AND DELIVERY TO PHOTOBIOREACTORS VIA MEMBRANE CARBONATION

(71) Applicants: Bruce Rittmann, Tempe, AZ (US); Klaus Lackner, Paradise Valley, AZ (US); Justin Flory, Scottsdale, AZ (US); Megha Patel, Chandler, AZ (US); Allen Wright, Gilbert, AZ (US)

(72) Inventors: Bruce Rittmann, Tempe, AZ (US); Klaus Lackner, Paradise Valley, AZ (US); Justin Flory, Scottsdale, AZ (US); Megha Patel, Chandler, AZ (US); Allen Wright, Gilbert, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 575 days.

(21) Appl. No.: 15/564,862

(22) PCT Filed: Apr. 7, 2016

(86) PCT No.: PCT/US2016/026414
§ 371 (c)(1),
(2) Date: Oct. 6, 2017

(87) PCT Pub. No.: WO2016/164563
PCT Pub. Date: Oct. 13, 2016

(65) Prior Publication Data
US 2018/0105780 A1    Apr. 19, 2018

Related U.S. Application Data
(60) Provisional application No. 62/144,018, filed on Apr. 7, 2015.

(51) Int. Cl.
C12M 1/00 (2006.01)
C12M 1/34 (2006.01)
B01D 53/04 (2006.01)

(52) U.S. Cl.
CPC ............ *C12M 21/02* (2013.01); *C12M 29/04* (2013.01); *C12M 41/26* (2013.01); *C12M 41/34* (2013.01);
(Continued)

(58) Field of Classification Search
CPC .............. B01D 53/04; B01D 2253/206; B01D 2257/504; C12M 21/02; C12M 29/04; C12M 41/26; C12M 41/34; Y02C 10/08
(Continued)

(56) References Cited

U.S. PATENT DOCUMENTS 5,281,254 A    1/1994  Birbara et al.
5,674,433 A *  10/1997 Semmens ........... B01F 3/04241
                                            261/120

(Continued)

FOREIGN PATENT DOCUMENTS

WO    WO 2010/036333    4/2010
WO    WO 2011/127172    10/2011

(Continued)

OTHER PUBLICATIONS

Wang et al., "Effect of pH growth and lipid content of Chlorella vulgaris cultured in biogas slurry", Chin J Biotech, Aug. 25, 2010, 26(8): 1074-1079 (Year: 2010).*

(Continued)

*Primary Examiner* — Liban M Hassan
(74) *Attorney, Agent, or Firm* — Lewis Roca Rothgerber Christie LLP

(57) ABSTRACT

The present application focuses on systems and methods that utilize one or more carbon dioxide ($CO_2$) sorbent substrates
(Continued)

and a swing cycle, e.g., a moisture swing cycle, to increase the partial pressure of the $CO_2$ in a gaseous feedstock, which is delivered through a membrane to a bioreactor, such as a membrane carbonation photobioreactor. Such systems and processes offer an effective means for concentrating and capturing $CO_2$ obtained from air and delivering the concentrated $CO_2$ to a photobioreactor through a membrane.

28 Claims, 6 Drawing Sheets

(52) U.S. Cl.
CPC ........ *B01D 53/04* (2013.01); *B01D 2253/206* (2013.01); *B01D 2257/504* (2013.01); *Y02C 20/40* (2020.08)

(58) Field of Classification Search
USPC .................................................... 435/292.1
See application file for complete search history.

(56) References Cited

U.S. PATENT DOCUMENTS

| | | | |
|---|---|---|---|
| 8,227,216 | B2 | 7/2012 | Hu et al. |
| 2007/0118916 | A1 | 5/2007 | Puzio et al. |
| 2008/0009055 | A1* | 1/2008 | Lewnard ................ B01D 53/84 435/262 |
| 2008/0087165 | A1* | 4/2008 | Wright ..................... A01G 9/18 95/51 |
| 2009/0180933 | A1* | 7/2009 | Kauling .............. B01F 3/04269 422/82.08 |
| 2009/0209015 | A1 | 8/2009 | Ramesha et al. |
| 2009/0294366 | A1* | 12/2009 | Wright ................... B01D 53/02 210/683 |
| 2010/0028962 | A1 | 2/2010 | Hu et al. |
| 2010/0151539 | A1 | 6/2010 | Franklin et al. |
| 2011/0065823 | A1 | 3/2011 | Lee et al. |
| 2011/0189075 | A1 | 8/2011 | Wright et al. |
| 2012/0070869 | A1 | 3/2012 | Hu et al. |
| 2012/0135478 | A1 | 5/2012 | Hu et al. |
| 2012/0171752 | A1 | 7/2012 | Chance et al. |
| 2012/0220019 | A1* | 8/2012 | Lackner ................. B01D 53/62 435/257.1 |
| 2012/0238002 | A1 | 9/2012 | Rittman et al. |
| 2013/0005022 | A1 | 1/2013 | Morris |
| 2014/0057321 | A1* | 2/2014 | Bae .......................... C12P 7/649 435/71.1 |
| 2014/0260968 | A1 | 9/2014 | Li et al. |
| 2014/0356275 | A1* | 12/2014 | Lackner ................. B01D 53/02 423/438 |
| 2015/0020683 | A1 | 1/2015 | Wright et al. |

FOREIGN PATENT DOCUMENTS

| | | | | |
|---|---|---|---|---|
| WO | WO 2012/016206 | | 2/2012 | |
| WO | WO-2012058662 | A2 * | 5/2012 | ............ C12M 21/02 |
| WO | WO-2013103748 | A1 * | 7/2013 | ............ B01D 53/62 |

OTHER PUBLICATIONS

Acién Fernández, G. et al., "Conversion of CO2 into biomass by microalgae: how realistic a contribution may it be to significant CO2 removal?", Applied Microbiology and Biotechnology, Nov. 2012 (available online Aug. 2012), 96(3), pp. 577-586.

Air Transport Action Group, "Reducing Emissions From Aviation Through Carbon-Neutral Growth From 2020", Developed for the 38th International Civil Aviation Organization Assembly, Sep.-Oct. 2013, 4 pages.

Chen, W. et al., "A high throughput Nile red method for quantitative measurement of neutral lipids in microalgae", Journal of Microbiological Methods, Apr. 2009 (available online Jan. 2009), 77(1), pp. 41-47.

Christi, Y., "Biodiesel from microalgae", Biotechnology Advances, May-Jun. 2007 (available online Feb. 2007), 25(3), pp. 294-306.

Davis, R. et al., "Techno-economic analysis of autotrophic microalgae for fuel production", Applied Energy, Oct. 2011 (available online May 2011), 88(10), pp. 3524-3531.

Fábregas, J. et al., "The cell composition of *Nannochloropsis* sp. changes under different irradiances in semicontinuous culture", World Journal of Microbiology and Biotechnology, Feb. 2004, 20(1), pp. 31-35.

Hikita, H. et al., "Absorption of carbon dioxide into aqueous sodium hydroxide and sodium carbonate-bicarbonate solutions", The Chemical Engineering Journal, 1976, 11(2), pp. 131-141.

Hu et al., "Optimization of growth and fatty acid composition of a unicellular marine picoplankton, *Nannocloropsis* sp., with enriched carbon sources," Biotech. Lett., 2003; 25: 421-425.

Hu, H. et al., "Response of growth and fatty acid compositions of *Nannochloropsis* sp. to environmental factors under elevated CO 2 concentration", Biotechnology Letters, Jul. 2006 (available online Jun. 2006), 28(13), pp. 987-992.

Huntley, M. et al., "CO2 Mitigation and Renewable Oil from Photosynthetic Microbes: A New Appraisal", Mitigation and Adaptation Strategies for Global Change, May 2007 (available online May 2006), 12(4), pp. 573-608.

International Preliminary Report on Patentability and Written Opinion for PCT/US2016/026414, dated Jul. 12, 2016.

International Preliminary Report on Patentability for PCT/US2011/045999, 14 pages, completed Jun. 26, 2012.

International Search Report for PCT/US2011/045999, dated Dec. 19, 2011.

International Search Report for PCT/US2016/026414, dated Jul. 12, 2016.

Kenyon et al., "Fatty acid composition of unicellular strains of blue-green algae," J. Bacteriology, 1972; 109: 827-834.

Kim, E. et al., "Direct membrane-carbonation photobioreactor producing photoautotrophic biomass via carbon dioxide transfer and nutrient removal", Bioresource Technology, Mar. 2016 (available online Dec. 2015), vol. 204, pp. 32-37.

Kim, H. et al., "Advanced Control for Photoautotrophic Growth and CO2-Utilization Efficiency Using a Membrane Carbonation Photobioreactor (MCPBR)", Environmental Science & Technology, Jun. 2011 (available online May 2011), 45(11), pp. 5032-5038.

Kim, H. et al., "Nutrient acquisition and limitation for the photoautotrophic growth of *Synechocystis* sp. PCC6803 as a renewable biomass source", Biotechnology and Bioengineering, Feb. 2011 (available online Sep. 2010), 108(2), pp. 277-285.

Kim, H. et al., "Responses of *Synechocystis* sp. PCC 6803 to total dissolved solids in long-term continuous operation of a photobioreactor", Bioresource Technology, Jan. 2013 (available online Oct. 2012) vol. 128, pp. 378-384.

Lackner, K. et al., "The urgency of the development of CO2 capture from ambient air", Proceedings of the National Academy of Sciences of the United States of America, Aug. 2012 (available online Jul. 2012), 109(33), pp. 13156-13162.

Lackner, K., "Capture of carbon dioxide from ambient air", The European Physical Journal Special Topics, Sep. 2009, 176(1), pp. 93-106.

Lee, K.-C. et al., "Effects of pH and precipitation on autohydrogenotrophic denitrification using the hollow-fiber membrane-biofilm reactor", Water Research, Apr. 2003 (available online Feb. 2003), 37(7), pp. 1551-1556.

Li, Y. et al., "Photosynthetic carbon partitioning and lipid production in the oleaginous microalga *Pseudochlorococcum* sp. (*Chlorophyceae*) under nitrogen-limited conditions", Bioresource Technology, Jan. 2011 (available online Jul. 2010), 102(1), pp. 123-129.

López Barreiro, D. et al., "Hydrothermal liquefaction (HTL) of microalgae for biofuel production: State of the art review and future prospects", Biomass and Bioenergy, Jun. 2013 (available online Feb. 2013), vol. 53, pp. 113-127.

Lu, W.C., "Microalgae-based Biofuel Technology Development in ITRI", ITRI Industrial Technology Research Institute, Oct. 6, 2009,

(56) References Cited

OTHER PUBLICATIONS

Presentation Slides, 34 pages, <http://www.phyco.org.tw/caa/04_Microalgae-based%20Biofuel%20Technology%20Development%20in%20ITRI.pdf>.

Martin, J. et al., "The membrane biofilm reactor (MBfR) for water and wastewater treatment: principles, applications, and recent developments", Bioresource Technology, Oct. 2012 (available online Mar. 2012), vol. 122, pp. 83-94.

Mata, T. et al., "Microalgae for biodiesel production and other applications: A review", Renewable and Sustainable Energy Reviews, Jan. 2010 (available online Aug. 2009), 14(1), pp. 217-232.

Novak, J. et al., "Inorganic carbon limited growth kinetics of some freshwater algae", Water Research, 1985, 19(2), pp. 215-225.

Ontiveros-Valencia, A. et al., "Managing the interactions between sulfate- and perchlorate-reducing bacteria when using hydrogen-fed biofilms to treat a groundwater with a high perchlorate concentration", Water Research, May 2014 (available online Feb. 2014), vol. 55, pp. 215-224.

Pierantozzi, R., "Carbon Dioxide", Kirk-Othmer Encyclopedia of Chemical Technology, Oct. 2003, vol. 4, pp. 803-822, John Wiley & Sons, Inc., Hoboken, NJ, USA.

Pyle, D. et al., "Producing docosahexaenoic acid (DHA)-rich algae from biodiesel-derived crude glycerol: effects of impurities on DHA production and algal biomass composition", Journal of Agricultural and Food Chemistry, Jun. 2008 (available online May 2008), 56(11), pp. 3933-3939.

Quinn, J. et al., "Geographical Assessment of Microalgae Biofuels Potential Incorporating Resource Availability", BioEnergy Research, Jun. 2013 (available online Nov. 2012), 6(2), pp. 591-600.

Radakovits, R. et al., "Genetic engineering of algae for enhanced biofuel production", Eukaryotic Cell, Apr. 2010 (available online Feb. 2010), 9(4), pp. 486-501.

Rittman, B. et al., "Pre-genomic, genomic and post-genomic study of microbial communities involved in bioenergy", Nature Reviews Microbiology, Aug. 2008 (available online Jul. 2008), 6(8), pp. 604-612.

Rittman, B., "The membrane biofilm reactor is a versatile platform for water and wastewater treatment", Environmental Engineering Research, Oct. 2007, 12(4), pp. 157-175.

Rittman, B., "The membrane biofilm reactor: the natural partnership of membranes and biofilm", Water Science & Technology, Feb. 2006, 53(3), pp. 219-225.

Rodolfi, L. et al., "Microalgae for oil: Strain selection, induction of lipid synthesis and outdoor mass cultivation in a low-cost photobioreactor", Biotechnology and Bioengineering, Jan. 2009 (available online Jun. 2008), 102(1), pp. 100-112.

Ryan, C., "Cultivating Clean Energy: The Promise of Algae Biofuels", Report by the Natural Resources Defense Council (ed. Alice Hartley), Oct. 2009, pp. 1-81.

Sheehan, J. et al., "A Look Back at the U.S. Department of Energy's Aquatic Species Program—Biodiesel from Algae", Technical Report by the National Renewable Energy Laboratory, Jul. 1998, pp. 1-328, Golden, CO, USA.

Sheng, J. et al., "Effects of temperature shifts on growth rate and lipid characteristics of *Synechocystis* sp. PCC6803 in a bench-top photobioreactor", Bioresource Technology, Dec. 2011 (available online Sep. 2011), 102(24), pp. 11218-11225.

Socolow, R. et al., "Direct Air Capture of CO2 with Chemicals: A Technology Assessment for the APS Panel on Public Affairs", Report by the American Physical Society, Jun. 2011, 100 pages.

Sukenik, A. et al., "Photosynthetic performance of outdoor Nannochloropsis mass cultures under a wide range of environmental conditions", Aquatic Microbial Ecology, Jun. 2009, 56(2-3), pp. 291-308.

Supplementary International Search Report for PCT/US2011/045999, dated Sep. 17, 2012.

Tang, Y. et al., "Hydrogen permeability of the hollow fibers used in H2-based membrane biofilm reactors", Journal of Membrane Science, Jul. 2012 (available online Mar. 2012), vol. 407-408, pp. 176-183.

Van Der Giesen, C. et al., "A Life Cycle Assessment Case Study of Coal-Fired Electricity Generation with Humidity Swing Direct Air Capture of CO2 versus MEA-Based Postcombustion Capture", Environmental Science & Technology, Jan. 2017 (available online Dec. 2016), 51(2), pp. 1024-1034.

Wang, T. et al., "Moisture-swing sorption for carbon dioxide capture from ambient air: a thermodynamic analysis", Physical Chemistry Chemical Physics, 2013 (available online Nov. 2012), 15(2), pp. 504-514.

Wang, T., et al., "Moisture Swing Sorbent for Carbon Dioxide Capture from Ambient Air", Environmental Science & Technology, Jun. 2011, 45(15), pp. 6670-6675.

Wigmosta, M. et al., "National microalgae biofuel production potential and resource demand", Water Resources Research, Mar. 2011, 47(4), 13 pages.

Williams, P. et al., "Microalgae as biodiesel & biomass feedstocks: Review & analysis of the biochemistry, energetics & economics", Energy & Environmental Science, Mar. 2010, 3(5), pp. 554-590.

Written Opinion for PCT/US2011/045999, 5 pages, dated Dec. 19, 2011.

Xu, F. et al., "Growth and fatty acid composition of *Nannochloropsis* sp. grown mixotrophically in fed-batch culture", Biotechnology Letters, Sep. 2004, 26(17), pp. 1319-1322.

Yu, Y et al., "Identification of the alga known as Nannochloropsis Z-1 isolated from a prawn farm in Hainan, China as Chlorella", World Journal of Microbiology and Biotechnology, Feb. 2007 (available online Jul. 2006), 23(2), pp. 207-210.

Zhao, H. et al., "Removal of multiple electron acceptors by pilot-scale, two-stage membrane biofilm reactors", Water Research, May 2014 (available online Feb. 2014), vol. 54, pp. 115-122.

Ziv-El, M et al., "Systematic evaluation of nitrate and perchlorate bioreduction kinetics in groundwater using a hydrogen-based membrane biofilm reactor", Water Research, Jan. 2009 (available online Oct. 2008), 43(1), pp. 173-181.

\* cited by examiner

SYSTEMS AND METHODS OF ATMOSPHERIC CARBON DIOXIDE ENRICHMENT AND DELIVERY TO PHOTOBIOREACTORS VIA MEMBRANE CARBONATION

CROSS-REFERENCE TO RELATED APPLICATION

This application is a national phase application under 35 U.S.C. § 371 of International Application No. PCT/US2016/026414, filed Apr. 7, 2016, which claims the benefit of U.S. Provisional Patent Application No. 62/144,018, filed Apr. 7, 2015, the contents of which applications are incorporated into the present application by reference.

A. FIELD OF THE INVENTION

The invention relates to membrane carbonation-photobioreactor systems. The invention also relates to systems that selectively remove gases from atmospheric air, particularly carbon dioxide ($CO_2$), and release them into controlled environments.

B. BACKGROUND OF THE INVENTION

Two and a half billion years ago, photosynthetic microorganisms completely transformed our planet by using solar energy to capture huge amounts of $CO_2$ from the atmosphere for growth and releasing oxygen ($O_2$). Today, these microalgae have the potential to produce fuels and products with significant economic value. Key to making microalgal technologies economically attractive is increasing the per-area productivity so that capital costs are offset by a large income stream. Despite atmospheric $CO_2$ levels rising at an alarming rate from anthropogenic fossil fuel combustion, current levels (~400 ppmv) present a significant limitation for technologies that rely on microalgal growth. One way to increase microalgal productivity is to deliver $CO_2$ at a concentration much higher than that in atmospheric air.

SUMMARY OF THE INVENTION

The present application focuses on systems and methods that utilize one or more $CO_2$ sorbent substrates and a swing cycle, e.g., a moisture swing cycle, to increase the partial pressure of the $CO_2$ in a gaseous feedstock, which is delivered through a membrane into a bioreactor, such as a membrane carbonation photobioreactor. Such systems and processes offer an effective means for concentrating and capturing $CO_2$ obtained from air and delivering the concentrated $CO_2$ into a photobioreactor through a membrane.

One aspect of the present disclosure relates to a system comprising a membrane bioreactor and moisture swing sorption (MSS) module where the MSS module supplies at least a portion of the gaseous feedstock to the bioreactor.

The terms "a" and "an" are defined as one or more unless this disclosure explicitly requires otherwise.

The terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, any of the present devices, systems, and methods that "comprises," "has," "includes" or "contains" one or more elements possesses those one or more elements, but is not limited to possessing only those one or more elements. Likewise, an element of a device, system, or method that "comprises," "has," "includes" or "contains" one or more features possesses those one or more features, but is not limited to possessing only those one or more features. Additionally, terms such as "first" and "second" are used only to differentiate structures or features, and not to limit the different structures or features to a particular order.

Furthermore, a structure that is capable performing a function or that is configured in a certain way is capable or configured in at least that way, but may also be capable or configured in ways that are not listed.

The feature or features of one embodiment may be applied to other embodiments, even though not described or illustrated, unless expressly prohibited by this disclosure or the nature of the embodiments.

Any of the present devices, systems, and methods can consist of or consist essentially of—rather than comprise/include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure may not be labeled in every figure in which that structure appears. Identical reference numbers do not necessarily indicate an identical structure. Rather, the same reference number may be used to indicate a similar feature or a feature with similar functionality, as may non-identical reference numbers.

DETAILED DESCRIPTION OF THE INVENTION

Figure 1A:
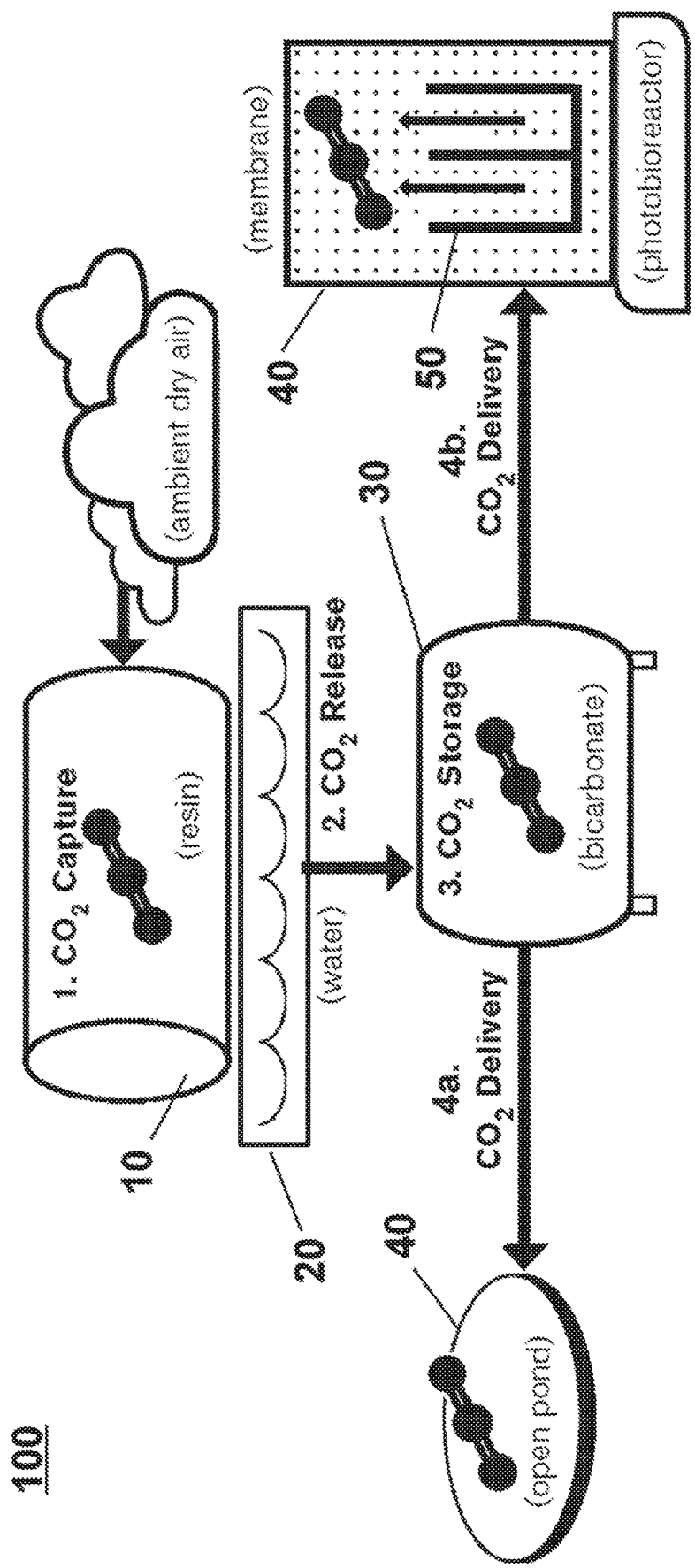
FIG. 1A illustrates a schematic of an embodiment in accordance with the present disclosure.

Referring now to the drawings and more particularly to FIG. 1A, shown there and designated by the reference numeral 100 is a first embodiment of an atmospheric $CO_2$ enrichment and delivery (ACED) system configured to concentrate $CO_2$ from air and transfer the $CO_2$ to an algae culture through a membrane system configured for diffusion-driven delivery of the $CO_2$. In the embodiment shown, system 100 comprises: (i) a collector 10 configured to capture $CO_2$ from air; (ii) a regeneration unit 20 configured to receive collector 10 within an enclosure, to regenerate collector 10 by causing it to release the captured $CO_2$; and to retain the released $CO_2$ in the form of dissolved $CO_2$; (iii) a storage-extraction unit 30 comprising a storage tank to store at least a portion of the released $CO_2$ from the regeneration unit 20 and configured to selectively extract the $CO_2$ from the storage tank for delivery to a bioreactor 40; (iv) a bioreactor 40 containing an algae-containing liquid; and (v) a membrane system 50 comprising one or more membranes configured for diffusion-driven delivery of a gas across the membranes to the liquid. Membrane system 50 is configured so that one side of each membrane interfaces with a gas flow comprising $CO_2$ from regeneration unit 20 and/or storage-extraction unit 30 and the other side of the membrane interfaces with a portion of the algae-containing liquid. In some embodiments, such a configuration can allow higher than ambient concentrations of $CO_2$ be delivered to an algae culture to boost productivity and do so in a more cost-effective way than delivery through traditional methods, such as gas sparging.

In some embodiments, collector 10 comprises a sorbent configured to selectively (or preferentially) capture $CO_2$ from air through the binding action of the sorbent, and regeneration unit 20 is configured to cause the captured $CO_2$ to be released from the sorbent thereby regenerating collector 10. In some embodiments, collector 10 comprises a sorbent that is attached to or coated on a substrate.

Figure 1B:
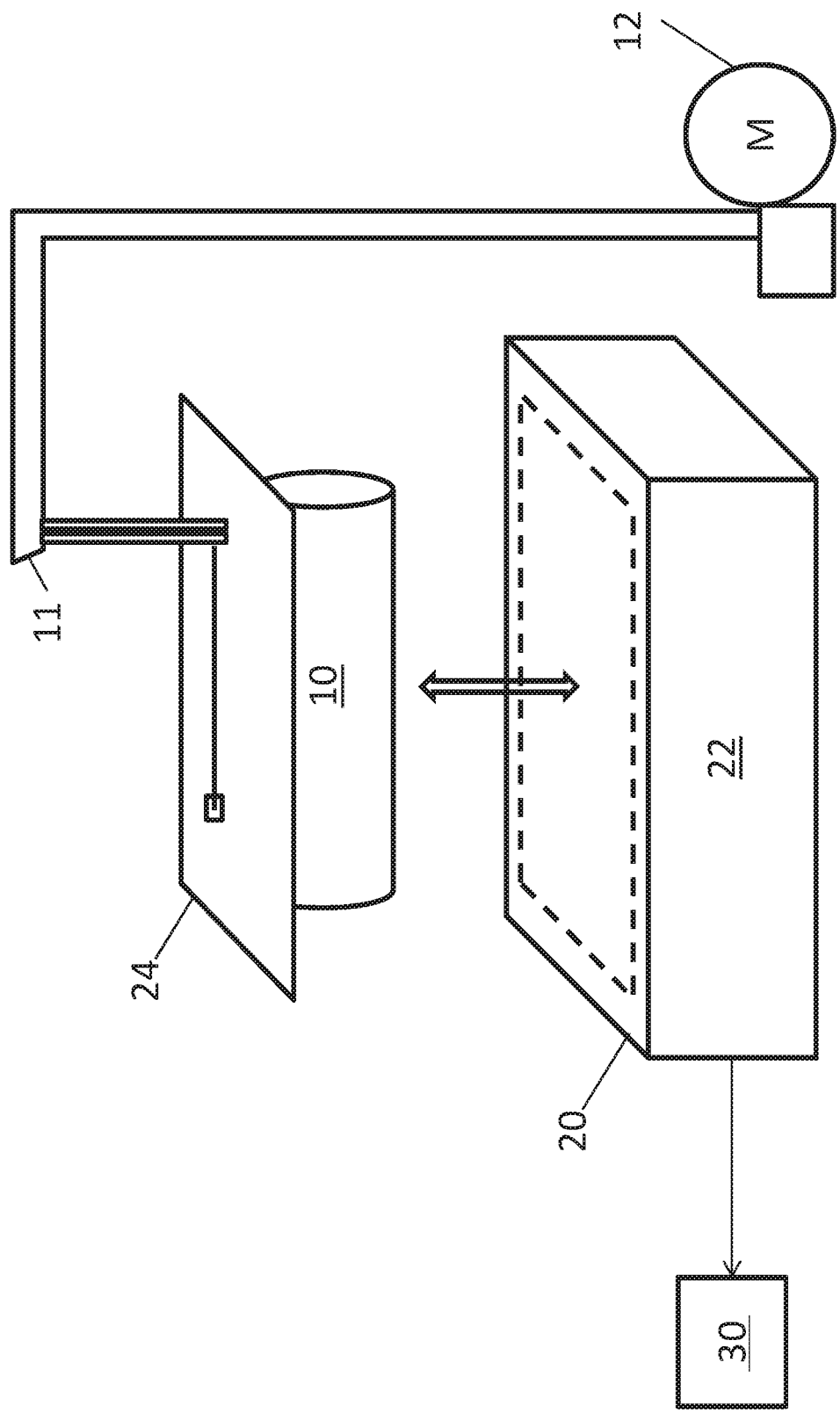
FIG. 1B illustrates a schematic of a collector and a regeneration unit in accordance with the present disclosure.

Collector 10 and/or regeneration unit 20 can be configured such that the collector can alternate between two environments, a first being one where collector 10 is exposed to outdoor/ambient air and the second being one where collector 10 is isolated from outdoor/ambient air (e.g., disposed within an enclosure of regeneration unit 20 which can be sealed). Collector 10 can be configured to move between at least two positions, namely, out of and into the regeneration unit 20, or an enclosure of regeneration unit 20 can be configured to move between at least two positions. For example, as shown in FIG. 1B, collector 10 can be coupled to a hoist 11 comprising a motor 12. Hoist 11 is configured to move collector 10 between a position that is within the enclosure 22 of regeneration unit 20 and a position where collector 10 is exposed to ambient/outdoor air, external to the enclosure 22. Enclosure 22 can comprise a cover 24 that is configured to move between two positions so that the enclosure can be opened to receive collector 10 and closed to seal enclosure and recover the absorbed $CO_2$. As shown, cover 24 can also be coupled to hoist 11 and configured to move with collector 10.

In other embodiments, collector 10 does not move between two positions but the enclosure of regeneration unit 20 is configured to move between two positions, such that the collector is disposed within the enclosure or disposed outside of the enclosure. And yet still in other embodiments, regeneration unit 20 can be configured to have one or more walls or sections of walls that form the enclosure and that move between two positions such that collector 10 disposed therein is exposed to outdoor/ambient air when the walls or section of walls are in a first position and the collector is isolated from outdoor/ambient air (e.g., the enclosure is sealed) when the walls are in a second position.

In some embodiments, the released $CO_2$, released in the regeneration unit 20, is transferred to membrane system 50. In some embodiments, the released $CO_2$ is transferred to the storage tank of storage-extraction module 30. Storage-extraction unit 30 is configured to produce a gas stream comprising a $CO_2$ concentration higher than ambient concentration with at least a portion of the $CO_2$ obtained from the solution in the storage tank. This gas stream is then fed to bioreactor 40 through membrane system 50. Through membrane system 50, the $CO_2$ is delivered by diffusion to the algae-containing liquid as needed. Of the $CO_2$ delivered to the microalgae, some fraction may be directly taken from the regeneration unit 20, storage-extraction unit 30, air, and/or other sources that were available at a specific site, such as an exhaust gas stream.

In some embodiments, the storage tank of extraction-storage unit 30 is included to account for discrepancies between the $CO_2$ pressure delivered by regeneration unit 20 and the $CO_2$ demand of the microalgal growth system. The $CO_2$ delivered by the regeneration subsystem 20 will fluctuate with temperature and humidity conditions, whereas the $CO_2$ demand of the bioreactor 40 varies with the seasons, temperature, and light levels. The extraction-storage unit 30 ensures the $CO_2$ released from regeneration unit 20 is always actively taken up, even if the algae demand is not sufficient, and there is always a reliable $CO_2$ supply for the microalgal growth system, even if atmospheric conditions were not conducive for capturing sufficient amounts of $CO_2$.

Figure 2:
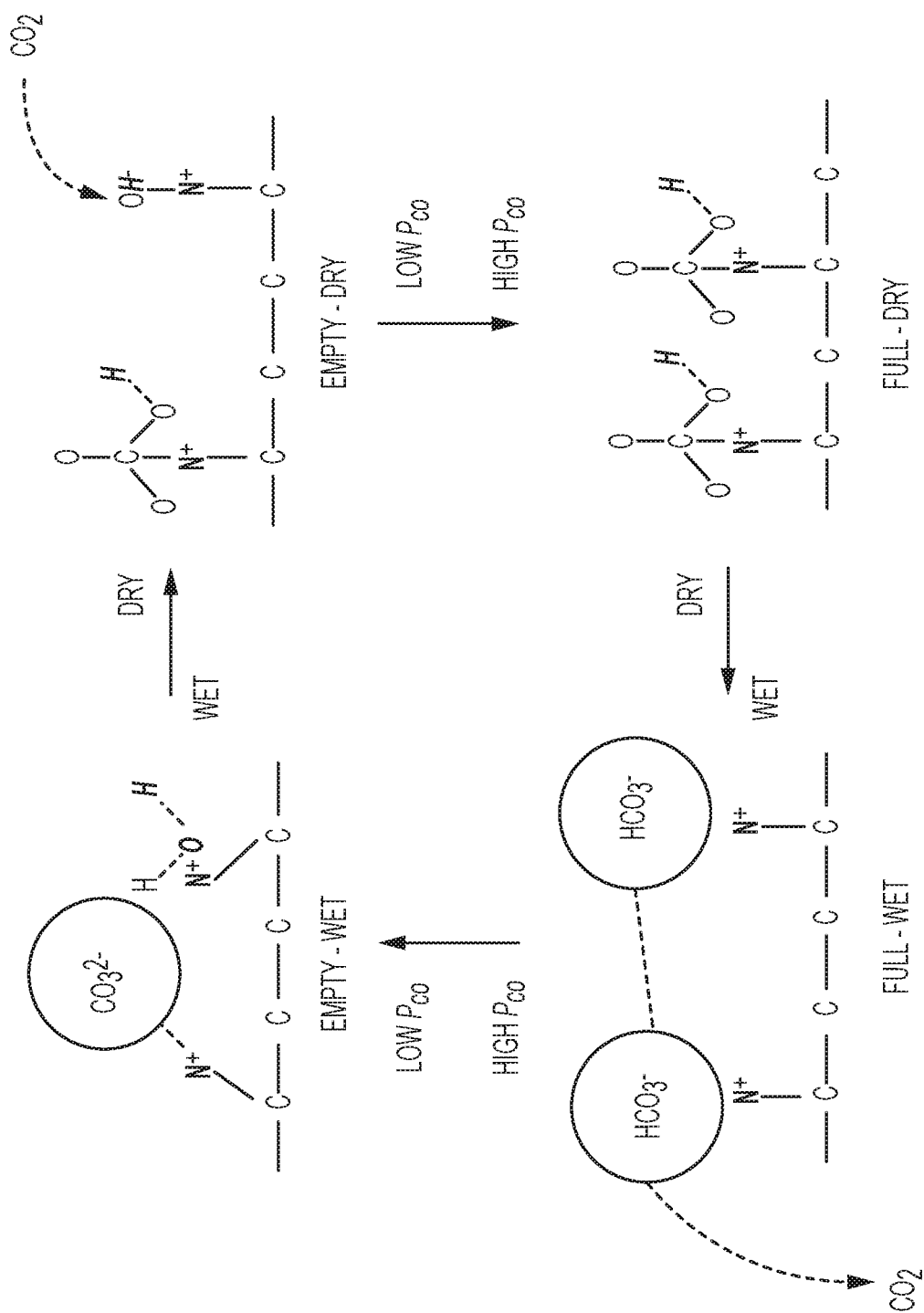
FIG. 2 illustrates the moisture-swing process with a quaternary amine sorbent. As shown in A), a wet resin binds a single $CO_2$ as a carbonate ion ($CO_3^{2-}$) for every two quaternary amines. B) As the resin dries, some quaternary amines bind with a hydroxide and others with a bicarbonate ion ($HCO_3^-$). C) If the dried resin is exposed to $CO_2$, a bicarbonate ion can form by the hydroxide ion reacting with $CO_2$. D) Exposing the dried resin to moisture after it has been exposed to $CO_2$, the water causes a release of $CO_2$ and regenerates the wet resin to (A).

As mentioned above, collector 10 is exposed to air and preferentially sorbs CO2. Collector 10 is able to capture CO2 through the action of a sorbent. For example, in some embodiments, polystyrene anion exchange resins, which are functionalized with quaternary ammonium ions, are used as the sorbent to capture atmospheric CO2 and to selectively release the CO2 using a wet-dry cycle, as shown in FIG. 2. This wet-dry cycle is in the following referred to as a moisture swing. Functionalized polystyrene anion exchange resins can contain about 0.5, 1, 1.5, 2, 2.5, 3, 3.5, 4 moles of quaternary ammonium ions per kilogram, or any value therebetween. In the loaded state, the charge of the quaternary ammonium ion is balanced by a bicarbonate ion (HCO3—). In the unloaded state the charge of two quaternary ammonium ions is balanced by a carbonate ion (CO3 2—). As shown in FIG. 2 the unloaded state still binds CO2, and, when compared to the state where all ions have been exchanged with hydroxide, it could still be considered half full. However, these states which contain less inorganic carbon than the carbonate state cannot be reached with a moisture swing. When an unloaded resin (FIG. 2), holding one carbon per two quaternary ammonium ions, is exposed to ambient air with low relative humidity, it dries and loads up with atmospheric CO2 until the anions are nearly all bicarbonates (FIG. 2). When the loaded resin is wetted or exposed to sufficient humidity within regeneration unit 20, the state holding one carbon for every two cations is preferred and the equilibrium shifts from bicarbonate to carbonate releasing CO2 from the sorbent (e.g., 2H-CO3—→CO2—+CO2+H2O) where it is captured into a contained environment for collecting the CO2. In some embodiments, a sweep gas flows through the regeneration unit 20 to carry the released CO2 to the storage-extraction unit and/or bioreactor 40. In some embodiments, the sweep gas is air.

The sorbent of collector 10 can be a porous material For example, the sorbent can be a membrane-type or sheet-like material that contains small active sorbent materials in its pores. In some embodiments, the sorbent of collector 10 comprises a felt-like material that comprises an ion-exchange material in a powder or fibrous form. In some embodiments, the felt-like material is disposed within a plurality of air-permeable baffles akin to a down blanket or quilt.

Figure 3:
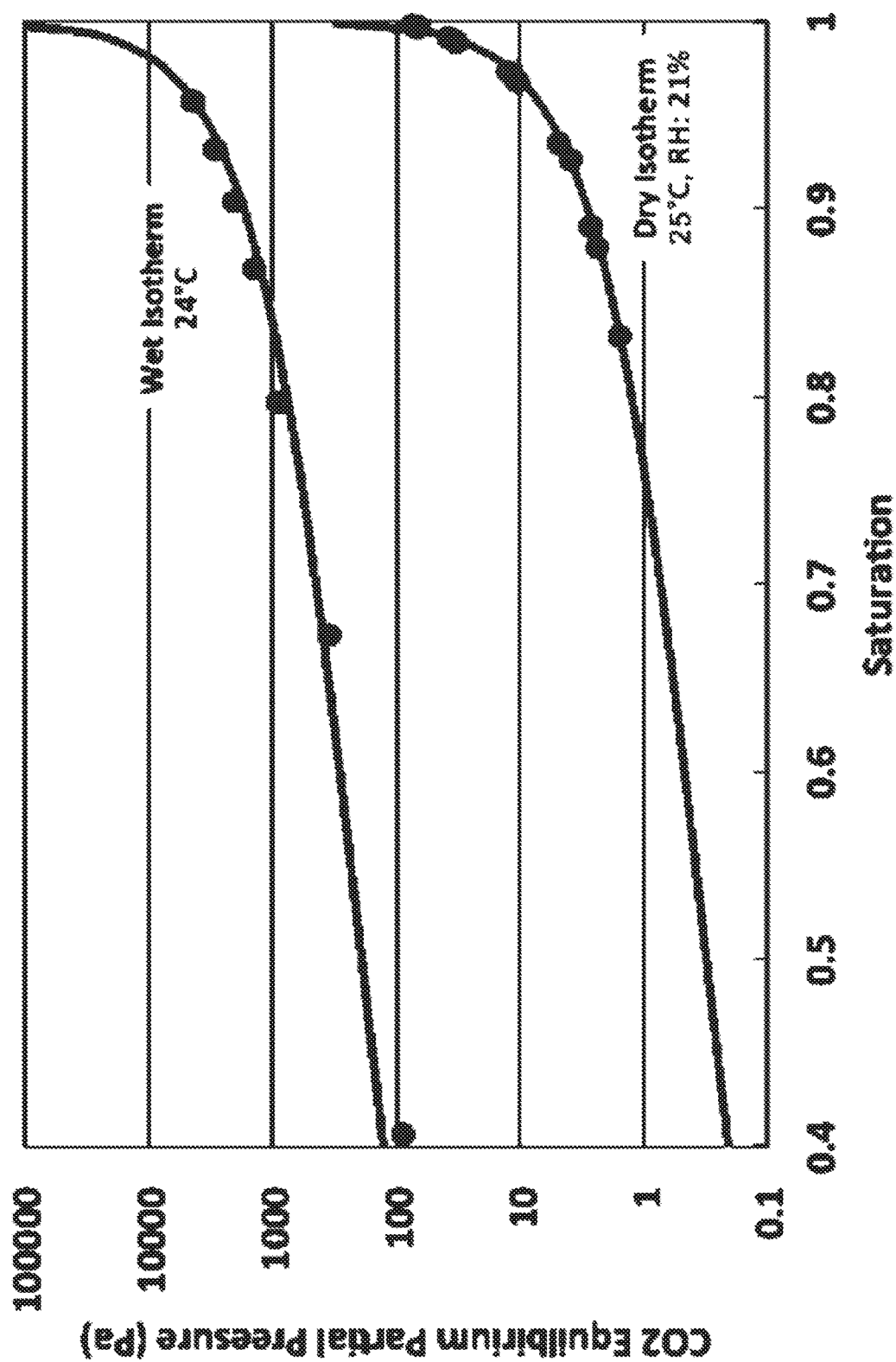
FIG. 3 shows isotherms of the equilibrium partial pressure (P) of $CO_2$ over a resin as function of the fraction (S) of the $CO_2$ binding sites occupied. P is 500 times larger for the wet resin than the dry resin. Data are fit to Langmuir isotherms, i.e., $P=P_0S/(1-S)$, where $P_0$ is a material property.

FIG. 3 shows that, at fixed temperature and loading, the equilibrium partial pressure of $CO_2$ over the resin increases 500 fold as the relative humidity changes from 21% to 100%, using moisture to swing the $CO_2$ partial pressure over the resin. In some embodiments, a plurality of collectors 10 can be used in system 100. In some embodiments, the regeneration unit 20 is configured to have a counter flow design where, a counter flow of a sweep gas advances from a first collector disposed in unit 20 to a second collector disposed in unit 20 and so on. The first collector holds less sorbed $CO_2$ than the second collector, and, similarly, when present, the second collector holds less sorbed $CO_2$ than a third collector. With a counter flow design, the last collector encountered by the sweep gas before the sweep gas exits the regeneration unit 20 is at the start of its regenerating process and thus holds the highest concentration of $CO_2$. The first collector encountered by the sweep gas after entering the regeneration unit 20 is at the end of its regenerating process and thus holds the lowest concentration of $CO_2$. The air in contact with each unit contains less $CO_2$ than the equilibrium partial pressure over the unit and thus $CO_2$ is released from each unit. However, the exit partial pressure of $CO_2$ will exceed the equilibrium partial pressure over the first nearly empty unit. In some embodiments, each collector 10 can advance through the regeneration process by way of a conveyor that moves opposite from the direction of the sweep gas. In some embodiments, the $CO_2$ partial pressure in a continuous gas stream can be amplified to 5000 Pa, or more than 100 times higher than in ambient air.

Regeneration unit 20 comprises one or more enclosures configured to receive one or more collector 10 and can be configured to regenerate the sorbent and cause release of $CO_2$ from the sorbent by causing one or more of a humidity increase, a temperature increase, and a pressure decrease at the surface of the sorbing substrate while within an enclosure of the regeneration unit. In some embodiments, regeneration unit 20 can comprise a buffer tank that comprises an aqueous solution that is applied to the sorbing substrate of collector 10, thereby regenerating the substrate and yielding a storage solution that can have a higher ratio of bicarbonate to carbonate than the initial solution. The storage solution is transferred to storage tank of storage-extraction unit 30. In some embodiments, $CO_2$ from the sweep gas is transferred to the storage solution, such as through a gas exchange membrane or a trickle bed exchanger or similar device.

In some embodiments, the storage solution has a lower pH than that of the initial aqueous solution. In some embodiments, the aqueous solution can comprise carbonate to bicarbonate ratio greater than or about 1, 2, 3, 4, 5, 6, 7, 8, 9, 10, 15, 20, 25, 30, 35, 40, 45, 50, 60, 70, 80, 90, or 100 or any value therebetween. In some embodiments, the aqueous solution can comprise bicarbonate to carbonate ratio greater than or about 1, 2, 3, 4, 5, 6, 7, 8, 9, 10, 15, 20, 25, 30, 35, 40, 45, 50, 60, 70, 80, 90, or 100 or any value therebetween. In embodiments, regeneration unit 20 can regenerate the sorbing substrate by applying water at about neutral pH to release bicarbonate and cause a decrease in the pH of the aqueous solution.

In some embodiments, storage-extraction unit 30 comprises at least one pump and one or more storage tanks for holding the storage solution and is configured to extract $CO_2$ from the storage tank solution for release into a gas stream either via a shift in pressure, temperature, or a combination thereof. The $CO_2$ concentration in the gas stream can be varied by the degree of the shift in pressure, temperature, or a combination thereof. In some embodiments, a gas stream can comprise $CO_2$ at 3% to 5%. Once the storage solution is effectively spent as a source of $CO_2$, it can be transferred to the buffer tank to be used as the aqueous solution to regenerate the sorbent. In some embodiments, storage-extraction unit 30 is configured to maintain a headspace above the bicarbonate/carbonate solution and to pump the gas from the headspace. A gaseous flow passes through the headspace having a $CO_2$ partial pressure that is lower than the vapor pressure of $CO_2$ for the carbonate/bicarbonate solution.

In some embodiments, collector 10 comprises a composite material comprising a sorbing surface. The sorbing surface can be adapted to impede salt build-up on the surface, which may occur as a result of repeat regeneration cycles. For example, the composite material can comprise a hydrophobic surface. In particular, a composite material comprising the sorbent can have a porous hydrophobic material disposed on the surface. The porous hydrophobic coating can comprise a polyolefin (e.g., a flashspun high-density polyethylene fibers such as Tyvek®), a fluoropolymer (e.g., polytetrafluoroethylene (PTFE) such as Teflon®), or a fluoropolymeric membrane (e.g., an expanded PTFE). The hydrophobic coating can be applied by vapor deposition, brush, dip or spray coating, or any method used to apply these hydrophobic coatings.

The surface area, shape, and dimensions of the sorbing surface of each collector 10 and the number of collectors 10 can depend on the $CO_2$ requirements of the algae culture being fed. In some embodiments, collector 10 comprises a wind-facing area that is at or less than 1 $m^2$. In some embodiments, collector 10 comprises a wind-facing area that is at or less than 10 $m^2$.

Bioreactor 40 comprises a reservoir configured to retain a culture of phototrophic microorganisms (such as an algae culture) in the reservoir and a membrane carbonation system 50 comprising one or more membranes configured for diffusion-driven delivery of $CO_2$. Bioreactor 40 can be open or closed. In FIG. 1A, the $CO_2$ from the storage tank is delivered to an open pond bioreactor via pathway 4a and/or delivered to a closed photobioreactor system via pathway 4b. In some embodiments, the one or more membranes are located in the lower light area of the reservoir. In some embodiments, a portion of the reservoir is blocked from a light source, and the one or more membranes are contained within the portion blocked from light. For example, the membrane system is placed near the middle of a closed photobioreactor, at the deeper levels of an open bioreactor, or behind a light shield, filter, or reflector in bioreactor 40 or in a separate enclosure through which the algae-containing media in bioreactor 40 is circulated. In some embodiments, the one or more membranes comprise a plurality of hollow fiber membranes through which the $CO_2$-containing gas flows. In some embodiments, the one or more membranes are a non-porous polypropylene tubes. In some embodiments gas flows in one end of the hollow fiber membranes that are closed at the other end. In other embodiments, a hollow fiber membrane is not closed at the other end and after the gas stream passes through the membrane in contact with the liquid medium, it is returned back to the storage tank for further enrichment and then circulated through the hollow fiber membrane again. In some embodiments, the tubes have an outer diameter of about 100 µm to 500 µm, such as 120, 140, 160, 180, 200, 220, 240, 260, 280, 300, 320, 340, 360, 380, 400, 425, 450, 500 µm, or any value or range therebetween. In some embodiments, each membrane can have a lumen diameter of 50 µm to 150 µm, such as 54, 58, 62, 66, 70, 74, 78, 80, 85, 90, 100, 110, 120, 130, 140, 150 µm or any value or range therebetween. In some embodiments, each membrane can have an outer diameter of about 200 µm and a lumen diameter of 67 µm. In some embodiments, each membrane can have an apparent $CO_2$ diffusivity of $10^{-4}$ $m^2/d$ to $10^{-6}$ $m^2/d$, such as about $10^{-5}$ $m^2/d$.

The conditions of the liquid media and of the membrane system are such to facilitate diffusion of $CO_2$ across the membrane at a rate substantially equivalent to the rate at which the culture consumes $CO_2$. Such conditions include the pH of the liquid media, the specific surface area of the membrane, the surface area of the membranes contacting the liquid media, and the partial pressure of the $CO_2$ on the one side of the membrane. For example, in some embodiments, the pH of the liquid media in bioreactor 40 is maintained between 7 to 10. For example, the pH of the liquid media is between 8.5 to 9.5 or between 8.8 to 9.2. In some embodiments, the pH of the liquid media is maintained at about a pH of 9. In other embodiments, the pH is greater than 10, such as 10.5, 10.7, 11 or any value or range therebetween, or less than 7, such as 6, 5, 4, 3.5, 3, 2.5, 2, 1.5, 1, 0.5, 0 or any value or range therebetween, to accommodate phototrophic microorganisms that favor those pH conditions. In some embodiments, the one or more membranes have a membrane specific surface area at or less than 25 $m^{-1}$, 20 $m^{-1}$, 18 $m^{-1}$, 15 $m^{-1}$, 12 $m^{-1}$, 5 $m^{-1}$, 1 $m^{-1}$, 0.5 $m^{-1}$ or any value or range therebetween. In some embodiments, the surface area of membranes interfacing with the fluid is between 0.005 to 0.025 $m^2$ per L of algae-containing liquid. In some embodiments, the gaseous flow received by the membrane system comprises between 3% and 5% $CO_2$, between 5% and 10% $CO_2$, between 10% and 30% $CO_2$, between 30% and 50% $CO_2$, between 50% and 80% $CO_2$, or between 80% and 100% $CO_2$. In some embodiments, the $CO_2$ transfer efficiency into the liquid media is at least 800/%, 85%, 900%, 95%, 98%, 99%, or 99.9%. Transfer efficiency, is the percentage of the $CO_2$ that moves across the membrane wall and into the reactor fluid rather than escaping to a gas phase.

In some embodiments, the concentration of dissolved inorganic carbon (DIC) in the liquid media is maintained at or below 10 mg DIC/L, such as at about 9.5, 9. 8.5, 8, 7.5, 7, 6.5, 6, 5.5, 5, 4.5, 4, 3.5, 3, 2.5, 2, 1.5, 1, or any value or range therebetween. In some embodiments, the concentration of DIC is maintained above 10 mg DIC/L, such as 11, 12, 13, 14, 15, 17.5, 20 or 25, or any value or range therebetween. In some embodiments, the concentration of DIC in the liquid media is maintained between 5 and 7 mg DIC/L. In some embodiments, the $CO_2$ concentration within the membranes is monitored continuously with infrared gas analyzers.

Figure 4:
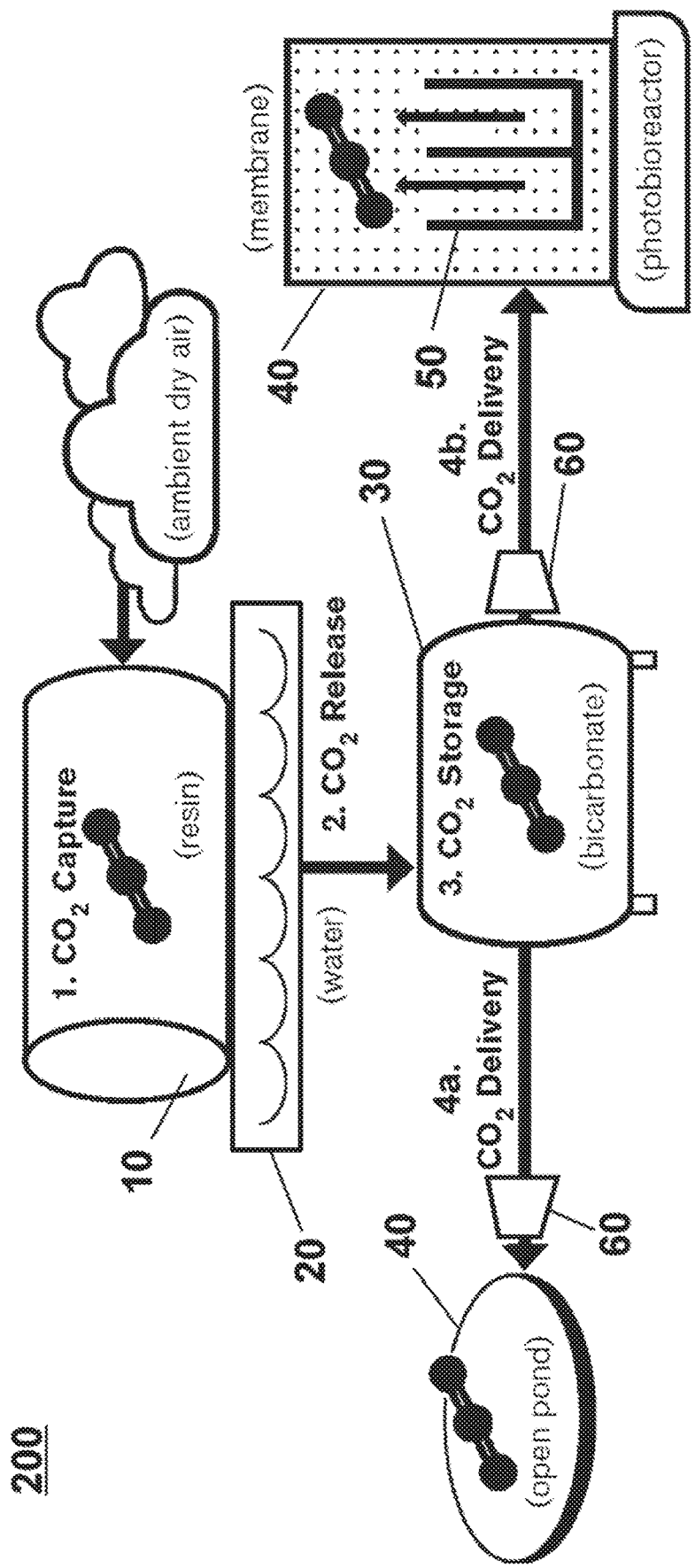
FIG. 4 illustrates a schematic of a second embodiment in accordance with the present disclosure.

Referring now to FIG. 4, shown therein and designated by the reference numeral 200 is a second embodiment of an ACED system configured to concentrate $CO_2$ from air and transfer the $CO_2$ to an algae culture through a membrane system configured for diffusion-driven delivery of the $CO_2$. Embodiment 200 is substantially similar to embodiment 100 described above, except that that system 200 further comprises a compressor 60 configured to compress $CO_2$, extracted from the storage solution and/or released from the substrate during regeneration, to gas pressures at or greater than 1, 2, 3, 4 or 5 atm, or any value therebetween. Such a compressor can be used to increase the partial pressure of the $CO_2$ for efficient delivery to bioreactor 40 through membrane system 50. In some embodiments, a gaseous flow from the headspace above the storage tank would flow into the compressor. In some embodiments, the gas produced during the regeneration process can flow into the compressor.

EXAMPLE

Figure 5:
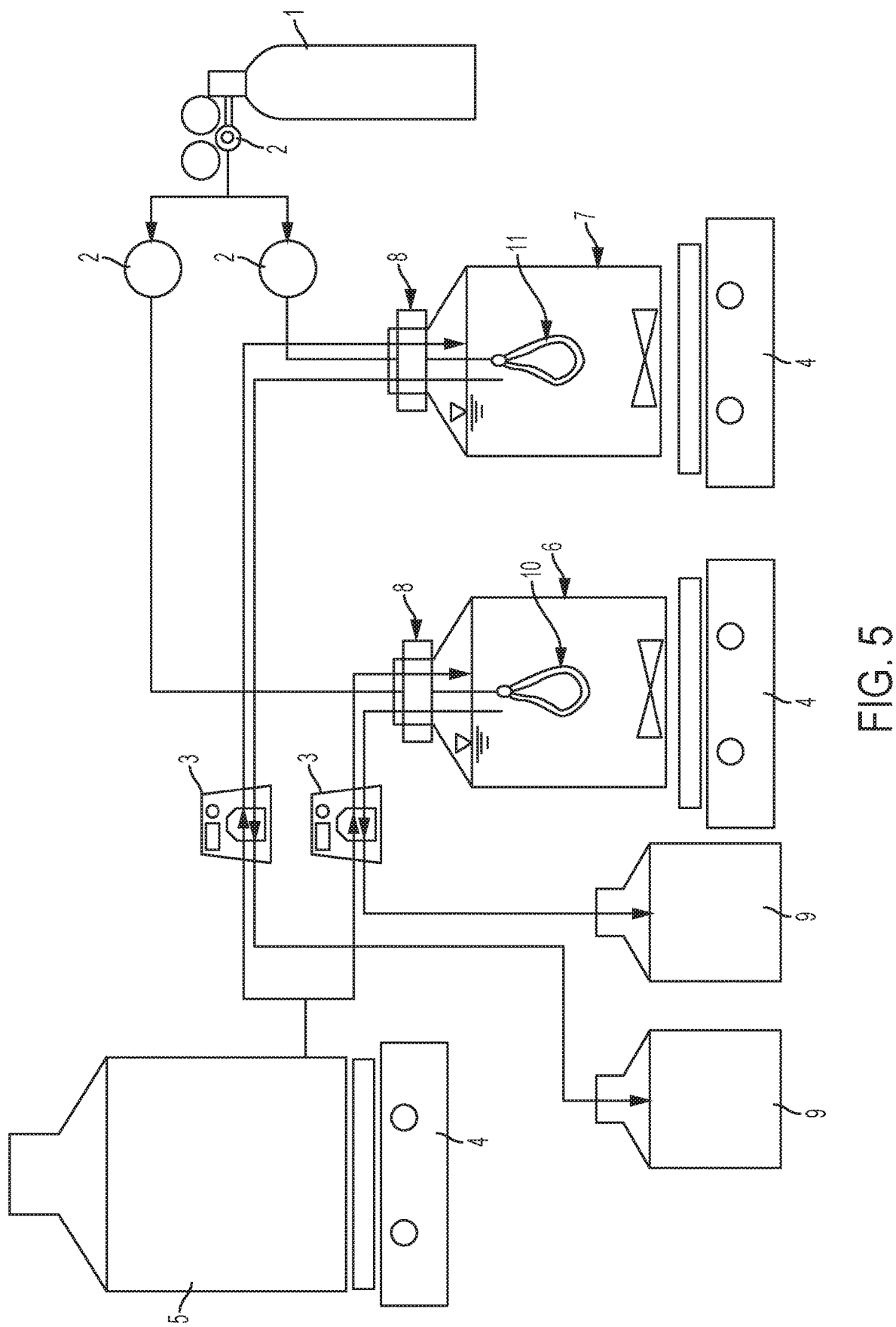
FIG. 5 illustrates schematic of two 5-L membrane carbonation photobioreactor co-systems set-up at the bench scale. The components include as follows: (1) $CO_2$ gas cylinder, (2) Pressure gauge, (3) Peristaltic pumps, (4) Magnetic stirrers, (5) Reservoir bottle for medium solution, (6 and 7) Photobioreactor vessels, (8) Light source, (9) Reservoir bottles for effluent, (10 and 11) Membrane Carbonation modules.

By way of example, a study was conducted to demonstrate the effectiveness of $CO_2$ taken up by an algae culture with a diffusion-delivery membrane system. FIG. 5 illustrates the experimental set-up. Membrane loops were placed near the middle of the photobioreactor so that they were not illuminated and did not accumulate significant biofilm. The systems were operated continuously to grow *Synechocystis* sp. PCC6883 with a modest external light intensity of 44 $W/m^2$ (~220 µE/$m^2$-sec), $CO_2$ pressure of about 1 atm, and different membrane specific surface areas <0.2 $m^{-1}$. Long-term performance at a pH controlled to near 9 demonstrated that $CO_2$ off-gas was zero, and at least 95% of the delivered $CO_2$ was invested into organic products of photosynthesis, with ≤5% in DIC in the effluent liquid. Thus, membrane carbonation delivered $CO_2$ with no waste and allowed good control at a suitable pH.

The above specification and examples provide a complete description of the structure and use of an exemplary embodiment. Although certain embodiments have been described above with a certain degree of particularity, or with reference to one or more individual embodiments, those skilled in the art could make numerous alterations to the disclosed embodiments without departing from the scope of this invention. As such, the illustrative embodiments of the present ACED systems and methods are not intended to be limited to the particular forms disclosed. Rather, they include all modifications and alternatives falling within the scope of the claims, and embodiments other than the one shown may include some or all of the features of the depicted embodiment. For example, components may be combined as a unitary structure and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not to be interpreted as including means-plus- or step-plus-function limitations, unless such a limitation is explicitly recited in a given claim using the phrase(s) "means for" or "step for," respectively.

The invention claimed is:

1. A system for growing phototrophic microorganisms comprising:
   a bioreactor comprising a microorganism-containing liquid and a membrane system;
   a collector comprising a sorbent for capturing $CO_2$ from air;
   a regeneration unit configured to:
   receive the collector within an enclosure,
   regenerate the sorbent by causing it to release sorbed $CO_2$, and
   capture the released $CO_2$;
   a storage tank coupled to the regeneration unit, the storage tank comprising a headspace, the storage tank being configured to receive the released $CO_2$ from the regeneration unit and containing at least a portion of the released $CO_2$ from the regeneration unit as a storage solution and at least a portion of the released $CO_2$ from the regeneration unit as a $CO_2$ gas, the headspace of the storage tank containing the $CO_2$ gas; and
   a pump coupled to the headspace and configured to pump the $CO_2$ gas from the headspace to a bioreactor via membrane system,
   the membrane system comprising one or more membranes configured for diffusion-driven delivery of a $CO_2$ gas across the one or more membranes to the microorganism-containing liquid of the bioreactor, a first side of a membrane of the one or more membranes configured to interface with a $CO_2$ gas stream from the storage tank and a second side of the membrane of the one or more membranes configured to interface with a portion of the microorganism-containing liquid in the bioreactor, the second side different than the first side.

2. The system of claim 1, where the collector comprises a composite material comprising the sorbent and having a hydrophobic surface.

3. The system of claim 1, where:
   the sorbent comprises a composite material having a surface, and
   a porous hydrophobic material is disposed on the surface.

4. The system of claim 3, where the porous hydrophobic material is one or more of the following: a polyolefin, a fluoropolymer, and a fluoropolymeric membrane.

5. The system of claim 1, where the pH of the liquid in the bioreactor is maintained between 7 to 10, between 8.5 to 9.5, or between 8.8 to 9.2.

6. The system of claim 1, where the pH of the liquid in the bioreactor is maintained at a pH between 10 to 11 or between 0 to 7.

7. The system of claim 1, where the membrane system is disposed in a lower light area within the bioreactor.

8. The system of claim 1, where the one or more membranes have a membrane specific surface area at or less than 25 $m^{-1}$, less than 20 $m^{-1}$, less than 18 $m^{-1}$, less than 15 $m^{-1}$, less than 12 $m^{-1}$, less than 5 $m^{-1}$, less than 1 $m^{-1}$ or less than 0.5 $m^{-1}$.

9. The system of claim 1, where a surface area of the one or more membranes interfacing with the liquid is between 0.005 to 0.025 $m^2$ per L of algae-containing liquid.

10. The system of claim 1, where a gaseous flow of the $CO_2$ gas received by the membrane system comprises between 3% and 5% $CO_2$, between 5% and 10% $CO_2$, between 10% and 30% $CO_2$, between 30% and 50% $CO_2$, between 50% and 80% $CO_2$, or between 80% and 100% $CO_2$.

11. The system of claim 1, wherein the regeneration unit is configured to regenerate the sorbent and release the CO2 from the sorbent by causing one or more of a humidity increase, a temperature increase, and a pressure decrease within the regeneration unit.

12. The system of claim 1, wherein the one or more membranes comprise a plurality of hollow fiber membranes through which the $CO_2$ from the storage tank passes.

13. The system of claim 1, where the sorbent is disposed on a sheet that is configured to be rolled and disposed in the regeneration unit and unrolled and exposed to the air.

14. The system of claim 1, where the sorbent is disposed on a sheet that is configured to be folded and disposed in the regeneration unit and unfolded and exposed to the air.

15. The system of claim 1, where the storage solution comprises bicarbonate and carbonate.

16. The system of claim 15, where the pump is configured to extract $CO_2$ from the storage solution by causing a shift in pressure, temperature, or a combination thereof.

17. The system of claim 16, where the pump is configured to cause a shift in a temperature of the storage solution.

18. The system of claim 16, where a gaseous flow passes through the headspace having a $CO_2$ partial pressure that is lower than a vapor pressure of $CO_2$ for the storage solution.

19. The system of claim 1, wherein the sorbent comprises a plurality of quaternary amines or carbonate perfused activated carbon.

20. The system of claim 1, further comprising a compressor configured to compress $CO_2$, either extracted from the storage solution or released from the sorbent during regeneration, to gas pressures at or greater than 1, 2, 3, 4, or 5 atm.

21. The system of claim 1, wherein the one or more membranes comprise a plurality of hollow fiber membranes configured to receive $CO_2$ from the storage tank.

22. The system of claim 1, wherein the bioreactor is configured to send gas, after the gas has passed through the membrane, to the storage tank to increase a $CO_2$ concentration and the storage tank is configured to receive the gas from the bioreactor and to increase its $CO_2$ concentration.

23. A method of growing an algae culture comprising:
   providing the system of claim 1;
   exposing a sorbing substrate comprising the sorbent to an atmosphere comprising $CO_2$ to capture a portion of the $CO_2$;
   causing a release, inside the enclosure, of the captured $CO_2$ from the sorbing substrate by altering pressure, humidity, temperature, or a combination thereof within the enclosure; and
   transferring a gas flow containing the released $CO_2$ to the one or more membranes disposed in the bioreactor comprising a culture of phototrophic microorganisms, wherein the concentration of $CO_2$ within the gas flow is higher than atmospheric concentration by at least 10-fold,
   wherein the released $CO_2$ disposed within the one or more membranes diffuses across the one or more membranes and into the culture of phototrophic microorganisms.

24. The method of claim 23, where the pH of the liquid in the bioreactor is maintained at about a pH of 9.

25. The method of claim 23, where causing the release of the captured $CO_2$ comprises applying an aqueous solution to the sorbing substrate.

26. The method of claim 23, comprising dissolving the $CO_2$ released inside the enclosure in an aqueous solution.

27. The method of claim 26, comprising storing the aqueous solution with the dissolved $CO_2$ in the storage tank.

28. The method of claim 26, comprising driving the $CO_2$ out of the aqueous solution and into the gas flow.

\* \* \* \* \*